(12) United States Patent
Törmälä et al.

(10) Patent No.: US 8,080,043 B2
(45) Date of Patent: Dec. 20, 2011

(54) BIOABSORBABLE, DEFORMABLE FIXATION MATERIAL AND IMPLANT

(75) Inventors: Pertti Törmälä, Tampere (FI); Harri Heino, Tampere (FI); Mikko Huttunen, Tampere (FI)

(73) Assignee: Bioretec Oy, Tampere (FI)

( * ) Notice: Subject to any disclaimer, the term of this patent is extended or adjusted under 35 U.S.C. 154(b) by 797 days.

(21) Appl. No.: 11/487,586

(22) Filed: Jul. 17, 2006

(65) Prior Publication Data

US 2007/0270852 A1 Nov. 22, 2007

(30) Foreign Application Priority Data

May 5, 2006 (FI) ..................................... 20065297

(51) Int. Cl.
*D04H 1/46* (2006.01)
*A61B 17/80* (2006.01)

(52) U.S. Cl. .......................... 606/286; 606/283; 442/401

(58) Field of Classification Search .................. 606/280, 606/286, 298, 299, 283; 442/382, 401, 402, 442/409
See application file for complete search history.

(56) References Cited

U.S. PATENT DOCUMENTS

| | | | |
|---|---|---|---|
| 4,512,038 A * | 4/1985 | Alexander et al. ......... | 623/23.75 |
| 4,968,317 A | 11/1990 | Törmälä et al. | |
| 5,529,736 A | 6/1996 | Shalaby et al. | |
| 5,868,746 A * | 2/1999 | Sarver et al. .................. | 606/281 |
| 6,171,338 B1 | 1/2001 | Talja et al. | |
| 6,605,553 B2 * | 8/2003 | Kuroiwa et al. .............. | 442/352 |
| 6,632,503 B1 * | 10/2003 | Shikinami et al. ............ | 428/131 |
| 6,692,497 B1 * | 2/2004 | Törmälä et al. ............... | 606/281 |
| 6,692,498 B1 * | 2/2004 | Niiranen et al. .............. | 606/70 |
| 6,908,582 B2 * | 6/2005 | Shikinami et al. ............ | 264/294 |
| 2003/0083745 A1 | 5/2003 | Pohjonen et al. | |
| 2004/0030341 A1 * | 2/2004 | Aeschlimann et al. ......... | 606/72 |
| 2004/0148014 A1 | 7/2004 | Nuutinen et al. | |
| 2004/0236327 A1 | 11/2004 | Paul et al. | |
| 2005/0059972 A1 * | 3/2005 | Biscup ........................... | 606/73 |
| 2005/0136764 A1 | 6/2005 | Sherman et al. | |
| 2005/0273104 A1 * | 12/2005 | Oepen et al. ................... | 606/69 |

FOREIGN PATENT DOCUMENTS

| | | |
|---|---|---|
| DE | 102004019846 A1 | 11/2005 |
| EP | 0 346 129 A1 | 12/1989 |
| EP | 0 449 867 B1 | 4/1994 |
| EP | 0321 176 B1 | 2/1995 |
| EP | 0 795 336 A1 | 9/1997 |

(Continued)

OTHER PUBLICATIONS

European Search Report—Dec. 28, 2007.

(Continued)

*Primary Examiner* — Thomas C. Barrett
*Assistant Examiner* — David Bates
(74) *Attorney, Agent, or Firm* — Venable LLP; Eric J. Franklin

(57) ABSTRACT

The invention relates to a bioabsorbable surgical osteosynthesis plate, operable to be secured by at least one fastener through at least one fastener opening formed in the plate to a bone. The osteosynthesis plate has first and second surfaces, and it is formed to one piece from a bioabsorbable polymer material that is oriented multiaxially and is substantially rigid and substantially deformable at a first thermochemical state. The plate comprises an oblique (diagonal) orientation gradient in relation to the direction of a reference axis of the plate.

16 Claims, 9 Drawing Sheets

FOREIGN PATENT DOCUMENTS

| | | |
|---|---|---|
| EP | 0 987 033 A1 | 3/2000 |
| GB | 2 307 179 A | 5/1997 |
| WO | WO 90/12550 A1 | 11/1990 |
| WO | WO-97/33017 A1 | 9/1997 |

OTHER PUBLICATIONS

Kazuhisa Bessho et al.; A Bioabsorbable Poly-L-Lactide Miniplate and Screw System for Osteosynthesis in Oral and Maxillofacial Surgery; American Association of Oral and Maxillofacial Surgeons; 1997; pp. 941-945.

Sylvie I. Ertel et al.; Evaluation of poly(DTH carbonate), a tyrosine-derived degradable polymer, for orthopedic applications; Journal of Biomedical Materials Research, vol. 29, 1995; pp. 1337-1348.

Eitenmüller et al.; Evaluation of a New High Strength Molecular Weight Polylactide Osteosynthesis Device; European Congress on Biomaterials; European Society for Biomaterials; Istituto Rizzoli, Bologna; 1986; p. 94.

Tunc et al.; Development of Absorbable, Ultra High Strength Poly(lactides); in Progress in Biomedical Polymers, Gebelein et al. ed.; 1992; pp. 239-248.

N. Inoue and M. Nishihara; Hydrostatic Extrusion Theory and Applications; 1985; pp. 331-362.

P. Törmälä et al; Ultra-high-strength absorbable self-reinforced polyglyclide (SR-PGA) composite rods for internal fixation of bone fractures: In vitro and in vivo study; Journal of Biomedical Materials Research, vol. 25, (1991) pp. 1-22.

Seppo Vainionpää et al.; Surgical Applications of Biodegradable Polymers in Human Tissues; Biodegrable Polymers in Surgery; *Pro. Polym. Sci.*, vol. 14, (1989); pp. 679-716.

\* cited by examiner

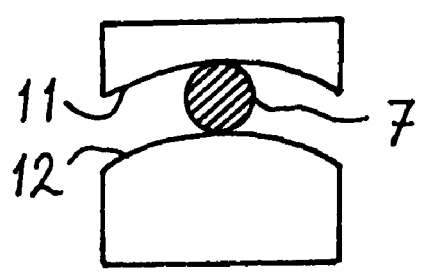
Fig. 3I
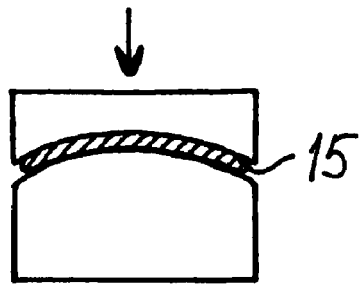
Fig. 3J
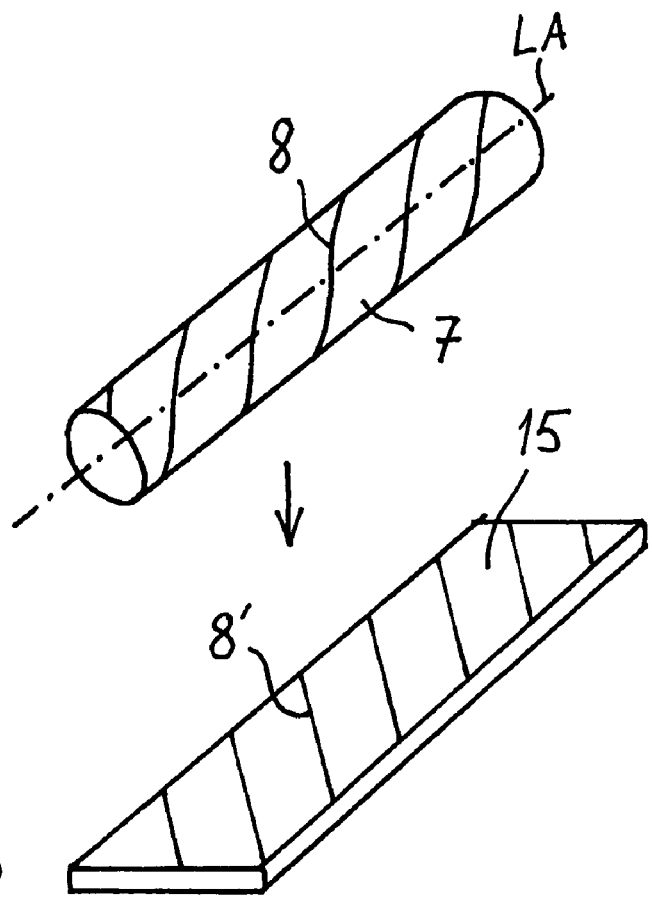
Fig. 4A
Fig. 4B

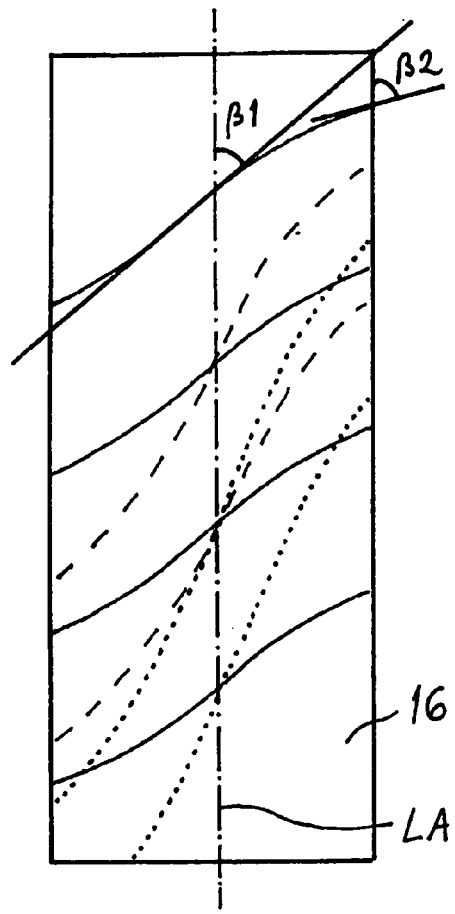
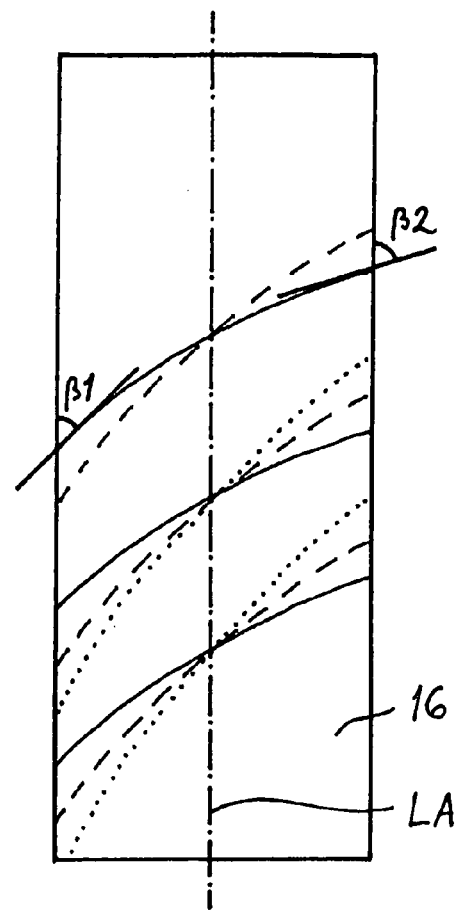
$\beta2 > \beta1$
Fig. 6A
$\beta2 > \beta1$
Fig. 6B
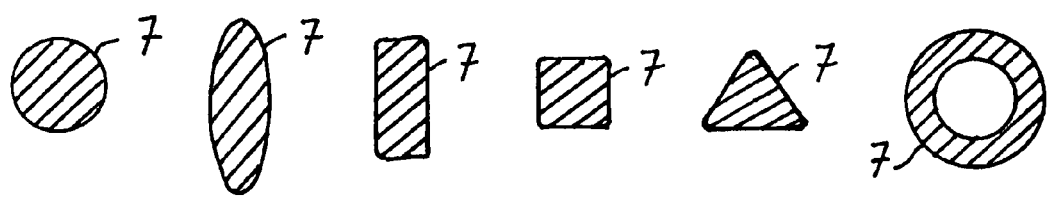
Fig. 7A  Fig. 7B  Fig. 7C  Fig. 7D  Fig. 7E  Fig. 7F

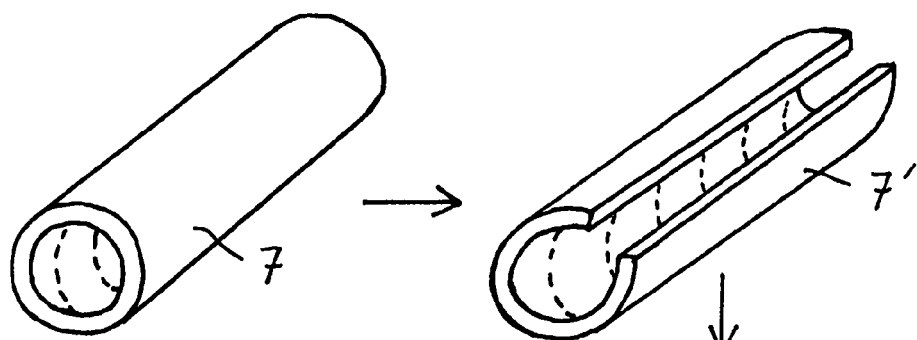
Fig. 9A   Fig. 9B
Fig. 9C
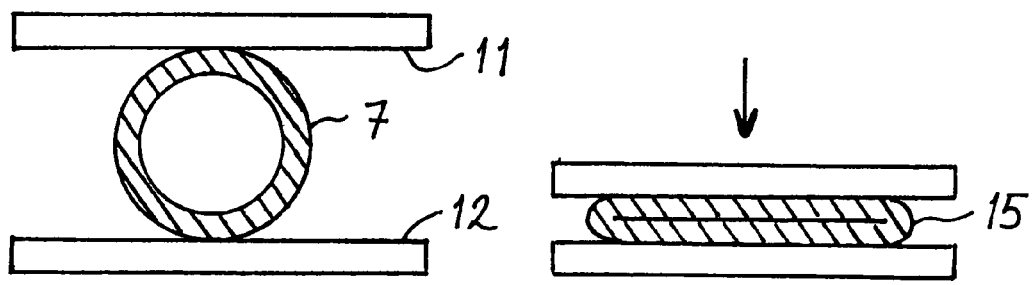
Fig. 9D   Fig. 9E

BIOABSORBABLE, DEFORMABLE FIXATION MATERIAL AND IMPLANT

FIELD OF THE INVENTION

The present invention relates to surgical materials and implants, method to manufacture such materials and implants and a method to use such materials and implants and, more particularly, bodily tissue fixation systems including bodily tissue fixation implants comprising bioabsorbable polymeric and/or composite plates.

BACKGROUND OF THE INVENTION

Because of shortcomings of metallic plates, bioabsorbable, polymeric plates have been developed for fracture fixation in bone surgery. E.g. elongated, bioabsorbable, six-hole plates were developed by Eitenmüller et al. for orthopaedic animal studies (European Congress on Biomaterials, Abstracts, Instituto Rizzoli, Bologna, 1986, p. 94). However, because of inadequate strength, some of the fracture fixation plates were broken in animal experiments.

U.S. Pat. No. 5,569,250 describes a biocompatible osteosynthesis plate operable for being enhanced in a substantially secured relation to a plurality of adjacent bone portions. The osteosynthesis plate is in a first configuration at a first thermochemical state and is operable to be converted to a second thermochemical state so that it may be deformed prior to fixation.

The first thermochemical state is typically room temperature (operation room conditions) and the second thermochemical state is typically an elevated temperature above Tg (glass transition temperature) of the polymer material (e.g. for polylactides between 50-60° C.). Accordingly, the plates of U.S. Pat. No. 5,569,250 must be changed from the first thermochemical state to the second thermochemical state, to be shaped (deformed) and thereafter they must be changed again back to the first thermochemical state prior to fixation. Because the thermal conductivity of polymeric materials is poor, the conversion of material to a second temperature is a slow process. Therefore, the clinical use of plates of U.S. Pat. No. 5,569,250 is tedious, slow and complex especially if the surgeon must shape the plate several times to make it fit exactly to the form of the bone to be fixed.

K. Bessho et al., J. Oral. Maxillofac. Surg. 55 (1997) 941-945, describe bioabsorbable poly-L-lactide miniplate and screw system for osteosynthesis in oral and maxillofacial surgery. Also these plates must be heated by immersion in a hot sterilized physiologic salt solution or by the application of hot air until they become plastic and can only then be fitted to the surface of the bone.

EP 0 449 867 B1 describes a plate for fixation of a bone fracture, osteotomy, arthrodesis etc. said plate being intended to be fixed on bone at least with one fixation device, like screw, rod, clamp or corresponding, wherein the plate comprises at least two essentially superimposed plates, so as to provide a multilayer plate construction, so that the individual plates of said multilayer plate construction are flexible so as to provide a change of form of said multilayer plate construction to substantially assume the shape of the bone surface in the operation conditions by means of an external force such as by hand and/or by bending instrument directed to said multilayer plate construction, whereby each individual plate assumes the position of its own with respect to other individual plates by differential motion along the coincident surfaces. The different plates can be manufactured of materials oriented and/or reinforced in different directions.

Although the said multilayer plate fits even the curved bone surface without heating of individual plates, the clinical use of multilayer plate is tedious, because the single plates easily slip in relation to each other before fixation. Additionally the thickness of multilayer plate system easily becomes too thick for cranio maxillofacial applications, causing cosmetic disturbance and increased risks for foreign body reaction.

EP 0 987 033 A1 describes a biodegradable and bioabsorbable implant material wherein its shape after deformation within ordinary temperature range can be fixed and maintained so that its shape can be easily adjusted at the site of operation, and it has substantially no anisotropy in view of strength. Particularly, it provides an implant material which can effect deformation such as bending or twisting within ordinary temperature range and has a shape-keeping ability to fix and maintain the shape after deformation as such, wherein molecular chains, domains of molecular chain assembly or crystals of the polymer are oriented along a large number of reference axes having random axial directions.

The small orientation units of molecular chains, domains of molecular chain assembly or crystals of EP 0 987 033 A1, form a non-continuous, random (non-directed) reinforcement into the material, analogous with the random short-fiber or whisker reinforcement. It should be advantageous to have in the oriented plate material a multiaxial continuous, directed, long-fiber like orientation, while long reinforcement units give usually better mechanical property combination for the material than short ones.

Random axial directions of oriented units could make the material structure unfavorable to resist shear (plate cutting) loads, which originate from the tendency of bone fragments to move (glide) in relation to each others in the direction of fracture plane (typically in the plane perpendicular to the flat surface and long axis of the plate).

Even if the implant material of EP 0 987 033 A1 can be bent or twisted within ordinary temperature range, it is manufactured with a complex non-continuous process including melt molding and two or more non-continuous forging (solid state molding) steps.

U.S. Pat. No. 6,221,075 and U.S. Pat. No. 6,692,497 describe bioabsorbable osteosynthesis plate and its surgical use. The plate is made of a material that is oriented uni- and/or biaxially and is substantially rigid and deformable at temperatures below the glass transition temperature of the material.

Uniaxially oriented plate material has good mechanical strength in the tensile mode but it is strongly anisotropic so that longitudinal splitting of the material is a risk, when mechanical forces are stressing the plate. On the other hand, biaxial orientation reduces the good tensile strength and shear strength of uniaxially oriented material.

Therefore there is a need of bioabsorbable (bioresorbable or biodegradable) oriented material or plate, which has the good shear load carrying capacity and good resistance against longitudinal splitting and which material or plate can be deformed below Tg of the material, yet dimensionally stable at said temperatures.

A need also exists for a material and plate, which in addition to aforementioned properties is strong, tough, and does not produce a substantial inflammatory response.

A need also exists for such a material and plate, which further can be deformed, yet is dimensionally stable, in operation room conditions, to facilitate the shaping of the plate.

A need also exists for such a material and plate, which has all the above-mentioned properties and can be deformed, yet is dimensionally stable in operation room conditions (in the first thermochemical state) to allow its fixation on bone without distortion of the configuration of the bone fragments to be fixed and which shaped plate is also dimensionally stable in tissue conditions (in the second thermochemical state), when fixed on bone surface to facilitate non-problematic bone fracture healing.

A need also exists for a bioabsorbable material and plate of the aforementioned type, which can be manufactured rapidly and effectively.

SUMMARY OF THE INVENTION

In this invention we have found surprisingly that the limitations of prior art materials and plates can be eliminated when a material piece is given multiaxial continuous orientation having a regular pattern as a result of some deforming steps.

We have found surprisingly that brittle and/or relatively weak bioabsorbable thermoplastic polymers, copolymers, polymer alloys or composites, with optional ceramic particulate fillers or fiber reinforcements, with Tg of the material above body temperature, which materials, such as plates, cannot be deformed at room temperature without a risk of breaking them or developing damages, like cracks or crazes into them, can be transformed into strong and tough plates with spiral orientation of the material preform and with working of the oriented preforms in the solid state to plate-like materials (or final plates) with an orientation gradient so that the materials or plates are deformable at room temperature and their mechanical properties can be effectively changed by changing the nature of the orientation gradient of preforms.

In the practice, the plate can be produced by making first an oriented, bioabsorbable preform with multiaxial spiral orientation. Spiral orientation is achieved e.g. by turning the ends of a preferably elongated, solid preform to opposite directions so that the preform twists itself along its long axis. As a consequence, spiral orientation means here that the orientation turns spirally around the long axis of the preform forming an orientation gradient inside of the preform. The orientation is strongest on the surface of the preform and decreases continuously deeper inside of the preform, while the turning deforms (orients) material most on the surface of the preform and least in the middle (core) of it. When compressing the preform, which contains the multiaxial spiral orientation, to a plate-like billet at a temperature above glass transition temperature, Tg, of the material but below the melting temperature, Tm, (if the material is partially crystalline), the orientation is retained in the plate-like billet as an orientation gradient, so that both surfaces of the plate-like billet have diagonal (oblique) orientation in relation to the direction of the long axis of the plate-like billet. The twisting can take place around a reference axis which is not necessarily the longest dimension of the preform. As a consequence of spiral orientation of the preform, the diagonal orientations on both flat surfaces of the plate-like billet are in opposite directions, so that their direction angles are equal but of opposite sign with respect to said reference axis. Because the steepness of the spiral orientation of the oriented preform decreases, when going inside of the preform from its surface, also the obliquity of the orientation of the compressed plate decreases (angles alpha and alpha' decrease) when going inside of the plate-like billet so that the orientation gradient is formed into the structure of the plate-like billet (or into the structure of the final plate). Accordingly, the diagonal (oblique) orientations on the both flat surfaces of the plate-like billet are directed more and more towards the direction of the long axis (or reference axis in general) of the plate-like billet, when going deeper into the structure of the plate-like billet. As a consequence, the plate-like billet (or the final plate) has a continuous, oblique orientation gradient with maximum of obliquity on the flat surfaces of the plate and minimum of obliquity (or practically no obliquity) in the middle of the plate, if the change of orientation is studied perpendicularly to the main plane of the plate within a confined area, it being understood that the orientation (angle) is not necessarily constant over the whole surface of the plate or over a single imaginary plane inside the plate.

Accordingly, the orientation gradient of the compressed plate-like billet comprises diagonal orientation, starting on both flat surfaces with maximal obliquity, but in opposite directions, and ending in the core of the plate-like billet with minimal obliquity. As a result, the plate-like billet (or the final plate), has an oblique orientation gradient in relation to the long axis (or reference axis) of the billet or plate. This gives for the billet and plate a tough structure, so that the billet or plate can be bended or twisted in the solid state and their structure resists effectively different mechanical loads in different directions as also the splitting (tear) between fixation device holes of the plate (which is made of the plate-like billet). Compared with plates where the orientation is uniaxial in the direction of the long axis throughout the thickness of the plate, a plate where the orientation changes throughout the thickness has increased strength in any short area that lies between the hole and the outer edge of the plate in the direction of long axis. The same is true for the general tendency of the plate to split in the direction of the long axis.

Spiral orientation means that a preferably elongated preform (with a circular, ellipsoidal, triangular, quadrangular, etc. cross-section) is turned around its long axis (or reference axis) in the solid state at a temperature above its Tg (but below its Tm, if any). This creates the spiral orientation gradient into the preform with the highest angle of the spiral (=the highest degree of spiral orientation) on the surface of the preform. The angle of the spiral decreases continuously in the direction to the middle of the preform so that the smallest angle of the spiral (near the value of zero degrees) is attained in the middle (core) of the preform and an orientation gradient is developed into the structure of the preform. Spiral orientation can be combined with longitudinal orientation if the preform is first oriented uniaxially in the direction of its long axis by drawing it in the direction of its long axis in the solid state at a temperature above its Tg (but below Tm, if any) and only thereafter it is turned around its long axis to create the spiral orientation gradient. Thereafter the preform is compressed in the solid state (at a temperature above its Tg, but below Tm, if any) to the form of a flat, plate-like billet, where the orientation gradient is retained as a diagonal orientation gradient. Finally, the plate-like billet is cooled below the Tg of the material.

Accordingly, the present invention describes oriented, rigid and tough materials and implants, like plates, with an oblique orientation gradient, which plates can be deformed at a first thermochemical state, like at room temperature in operation room conditions, prior to implantation, and which implants retain their deformed (shaped) form so well also in the second thermochemical state at body temperature in tissue conditions, when implanted on bone, that they keep the fixed bone fragments essentially in the desired position to facilitate bone fracture healing.

The first thermochemical state can be any temperature below Tg of the material down to the room temperature ($T_{RT}$) area because plates with an orientation gradient retain their properties of being substantially deformable and substantially rigid at such temperatures.

An advantage of the present invention is to provide a low profile oriented biocompatible plate implant with orientation gradient structure and with sufficient strength to be operable for enhancing a substantially secured relation between a plurality of adjacent bone portions. Further advantages of the invention are to provide a biocompatible plate implant of the above-mentioned type, which
- is bioresorbable over a desired period of time while not generating a substantial inflammatory response,
- is relatively rigid at a first thermochemical state, but is also relatively deformable at said first thermochemical state prior to implantation,
- is repetitively deformable at the said first thermochemical state prior to implantation,
- can be easily and inexpensively manufactured with continuous, semi-continuous or non-continuous processes, and
- is operable to enhance a secured relation between the oriented biocompatible fixation device (plate) and one or more adjacent bone portions.

The present invention, in one embodiment thereof, provides a low-profile oriented biocompatible osteosynthesis plate with an oblique orientation gradient structure and operable for being enhanced in a substantially secured relation to a plurality of adjacent bone portions. The osteosynthesis plate includes an elongated section having a top face and a bottom face, which elongated section is operable for traversing a fracture site or osteotomy site for subsequent fixation to adjacent bone portion. The oriented osteosynthesis plate further includes a plurality of fastener openings disposed between the top face and bottom face to allow the location of a plurality of surgical fasteners therethrough. The osteosynthesis plate further may include means disposed upon the elongated section to permit the formation of additional fastener openings therethrough during a surgical procedure at the discretion of the surgeon. The osteosynthesis plate is relatively rigid at a first temperature and is deformable in three dimensions, yet dimensionally stable, at said first temperature. The osteosynthesis plate retains a deformed position at said first temperature in operation conditions, but can be subsequently returned to its original configuration by redeformation at said first temperature, at said first thermochemical state. As such, the oriented osteosynthesis plate of the present invention may be repeatedly deformed and returned to its original configuration at said first temperature (first thermochemical state) in order to contour the osteosynthesis plate precisely to a desired configuration through successive deformations.

The present invention also includes surgical, bioabsorbable (bioresorbable) fixation devices, like bone screws or tacks, which are operable to be inserted through fastener openings disposed within the oriented osteosynthesis plates of the present invention. As such, the present invention contemplates a bone stabilization device including a bioabsorbable osteosynthesis plate with diagonal orientation gradient structure and bioabsorbable surgical fastener(s).

The present invention also provides a method for forming a low-profile oriented biocompatible, surgical bioabsorbable osteosynthesis plate including the steps of formation of a longitudinal preform, its optional longitudinal (uniaxial) orientation (drawing), its spiral orientation, and formation of an oriented, osteosynthesis plate-like billet from the preform with spiral orientation gradient by a suitable working method, and finishing, surface cleaning, sterilization and packaging of the plate.

The present invention also provides a method for enhancing a substantially secured relation between a plurality of adjacent bone portions including the steps of providing a low-profile, biocompatible, osteosynthesis plate with an oblique (diagonal) orientation gradient as explained above, positioning such a plate upon a plurality of adjacent bone portions, providing a plurality of surgical fasteners for enhancing a fixed relation between the oriented osteosynthesis plate and at least one adjacent bone portion, positioning the plurality of surgical fasteners within a plurality of fastener openings upon the oriented osteosynthesis plate and substantially securing the plurality of surgical fasteners into the adjacent bone portions.

During orientation, polymer molecules or their segments tend to align with their long axis in the direction of orientation. A description of molecular background of orientation of polymeric materials and of its physical characterization is given e.g. in U.S. Pat. No. 4,968,317 and in references therein. The effects of orientation are most pronounced in partially crystalline polymers, but it is also possible to orient non-crystalline (amorphous) polymers, as has been described in PCT/FI96/00511.

BRIEF DESCRIPTION OF THE DRAWINGS

Other advantages of the present invention will become apparent to one skilled in the art upon reading the following specification and the following drawings.

FIGS. 4A-4B show schematically how the spiral orientation on the surface of a cylindrical preform, with a spiral orientation gradient, (FIG. 4A) is retained as a diagonal (oblique) orientation on the surface of a plate-like billet (FIG. 4B), which is compressed of the oriented preform, FIGS. 6A-6B show schematically the variation of the diagonal orientation gradient structure in an oriented plate according to the invention in a direction perpendicular to the long axis, FIGS. 7A-7F show different cross-section geometries of polymeric or composite preforms, FIGS. 9A-9C show schematically another method of forming a flat plate-like billet with oblique orientation, FIGS. 9D-9E show schematically still one method of forming a flat plate-like billet starting from the preform of FIG. 9A.

DESCRIPTION OF THE PREFERRED EMBODIMENT

For the purpose of promoting and understanding of the principles of the invention, reference will now be made to the preferred embodiments of the present invention. It will nevertheless be understood that no limitation of the scope of the invention is thereby intended, such alterations and further modifications, and such further applications of the principles of the invention therein being contemplated as would normally occur to one skilled in the art to which the invention relates.

Figure 1:
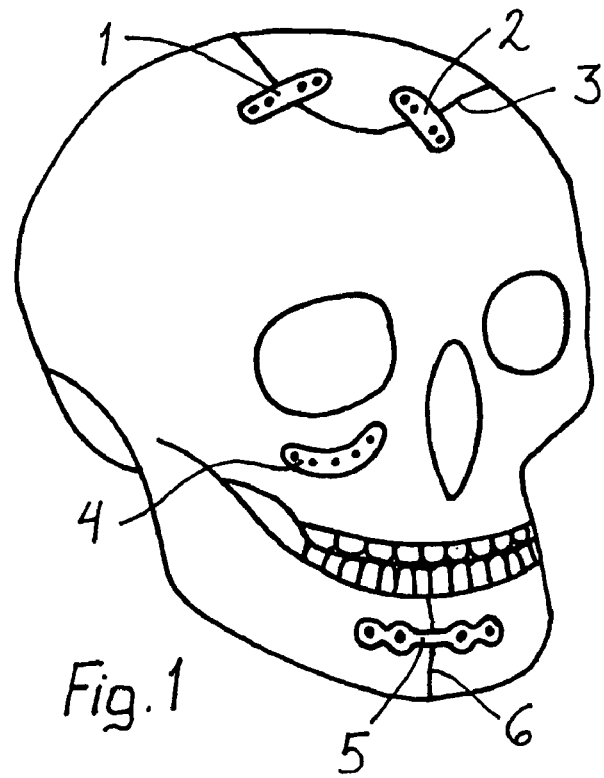
FIG. 1 shows a perspective view of a plurality of osteosynthesis plates according to the present invention, shown in association with the repair of cranio maxillofacial or mandibular fractures.

Referring to FIG. 1, there are shown biocompatible, bioabsorbable osteosynthesis plates 1-2, 4 and 5 with a diagonal orientation gradient according to preferred embodiments of the present invention. The oriented biocompatible osteosynthesis plates are shown as being disposed over bone fractures or osteotomies 3 and 6. It will be appreciated that osteosynthesis plates of this invention, like plates 1-2, 4 and 5, may be of any size or shape as will be hereinafter discussed. Further, the osteosynthesis plate, like 1-2, 4 and 5, may also be deformable and rigid at a first thermochemical state, like in operation room conditions. "A thermochemical state" as used in describing the present invention is defined according to U.S. Pat. No. 5,569,250 as a combination of thermal and chemical conditions resulting from exposure to certain thermal and chemical environments like room temperature and operation room atmosphere, respectively. Although one type of change in thermochemical state occurs by a change of temperature alone, changes in thermochemical state of an oriented biocompatible implant of the present invention should be understood as not limited only to changes in temperature.

Preferably, the oriented biocompatible, bioabsorbable osteosynthesis plates of this invention are relatively rigid at both room temperature and at human body temperature and they are deformable at temperatures (like at room temperature) below Tg of the material from which the oriented biocompatible osteosynthesis plates are made. Therefore there is no need to heat the plates of this invention to temperatures above Tg of the material, as must be done with many prior art plates. Because of the diagonal orientation gradient of the materials of the invention, they express the substantial rigidity and substantial deformability in all temperatures between Tg of the material and room temperature which also include human body temperature (in certain cases even at temperatures below room temperature).

Importantly, the oriented biocompatible, bioabsorbable osteosynthesis plates of this invention are formed by methods such that they are dimensionally stable and deformable in operation conditions at room temperature and/or at any temperature above room temperature (first thermochemical state) but at or below body temperature (second thermochemical state). As used herein, the term "dimensionally stable" means that the biocompatible, bioabsorbable osteosynthesis plates with a diagonal orientation gradient are able to retain substantially the same configuration at either of said two thermochemical states so that the oriented osteosynthesis plates facilitate bone fracture healing by keeping the fractured pieces in the proper position in relation to each others.

The rigidity, deformability and the dimensional stability are due to the manufacturing process of plates with a diagonal orientation gradient, which is also discussed below.

The oriented biocompatible osteosynthesis plates, like those of FIG. 1, are typically formed from spiral oriented bioabsorbable polymer, copolymer, polymer alloy or composite (with or without particle filler or fiber reinforcement) preforms. Examples of such materials are e.g. lactide (80-85 mol-%) and glycolide (15-20 mol-%) copolymers which have glass transition temperatures (Tg) between 50° C. and 65° C.

Osteosynthesis plates with a diagonal orientation gradient made using bioabsorbable materials and in the manner discussed below will retain a substantial proportion of their strength after the first several weeks or months after implantation when this strength must be relatively high.

Osteosynthesis plates with a diagonal orientation gradient may be done of partially crystalline or non-crystalline (amorphous) materials. The oriented osteosynthesis plates of this invention are operable to stabilize a plurality of bone portions for a period of from one to several months following implantation and yet be completely resorbed after one year or several years following implantation, depending on such factors as chemical composition and molecular weight of the bioabsorbable polymeric material, implant size and geometry or the position of the implant in human body. Accordingly, the resorption time can be tailored to be fast or slow. Slow resorption is advantageous in the case of slowly healing fractures and a relatively fast resorption of the bioabsorbable material reduces the unwanted cosmetic appearance as well as growth restriction in pediatric patients.

It will be appreciated that the oriented biocompatible, bioabsorbable osteosynthesis plates of this invention may have a variety of sizes and/or shapes as hereinafter discussed and may also be made of a bioabsorbable material of different origins. In addition, the oriented biocompatible osteosynthesis plates of this invention are preferably both rigid and deformable at room temperature (below Tg of the material) and at human body temperature (also below Tg of the material).

Suitable plate geometries of osteosynthesis plates, which can be applied in manufacturing of the osteosynthesis plates of this invention are given e.g. in prior art, e.g. in U.S. Pat. No. 6,221,075 and in references therein.

The osteosynthesis plates of this invention are typically flat and can include one or more fastener openings and/or portions where the surgeon can form additional fastener opening(s) e.g. by drilling. These flat plates can be formed to three-dimensional contour specific for a surgical application also during the manufacturing process to minimize the need of bending the plate during surgical operation.

The flat plates of this invention are provided to be in a "low-profile" construction, that is, of a preferably thin nature so as to cause a minimum protrusion above the bone surface to which they are applied. In this regard, the term "low profile" will be used to refer to a construction in which the width is greater than about four to six times the height of the plate. For example, the plate may typically have a width of 4-8 mm, a length of between about 10 mm to 80 mm (or even up to ca. 200 mm) and a height (thickness) of about 0.3 mm to 3.5 mm.

The flat plates of this invention are also characterized by their ability to be deformed, without heating them above Tg of the plate material, during a surgical procedure to be conformed to the contour of the bone surface to which it is applied. This feature is especially useful in the surgical repair of bone surfaces having curvatures, including the maxillofacial bones of the craniofacial skeleton, but also bone surfaces in many other parts of human body, like in the extremities, in the thorax and in the spine.

During deformation, the flat plates of this invention are deformed, by manipulating the plate by hands or with special manipulating device(s), in a first thermochemical state, i.e. in operation room conditions during a surgical operation. Accordingly, there is no need to convert the plate before deformation to a higher temperature, using e.g. a heating device, as is needed e.g. in prior art U.S. Pat. No. 5,569,250. The deformed plate of this invention will then be located into the second thermochemical state when fixed on bone to fixate the bone fracture. More preferably, because the flat osteosynthesis plates of this invention are formed by a method which causes the plates to be deformable, ductile, rigid and dimensionally stable during operation in operation room conditions, in the first thermochemical state, the flat plates of this invention are able to return to their original configuration upon deforming them again in operation room conditions. As such, it will be appreciated that this ability allows the flat plates to be repetitively deformed and returned to their original configuration, thus allowing for successive rapid attempts by a surgeon during a surgical procedure to conform the flat plates in three dimensions to correspond as closely as possible to the contours of the bone surface to which the flat plates will be applied. These successive deformations can be done conveniently and rapidly in operation room by operation table without heating and cooling conversions, which are needed in bending of prior art plates, e.g. like those of U.S. Pat. No. 5,569,250.

The formation of additional fastener openings through the flat plates of this invention may be accomplished simply drilling through the material from which the flat plates are made as discussed above. Such drilling is performed through means well known to those skilled in the art. The flat plates are then operable to accept a plurality of surgical fasteners, such as biocompatible and bioabsorbable (bioresorbable) bone screws or tacks, which may be constructed of the same material as the flat plates, or may alternatively be made of another bioabsorbable material.

Figure 11:
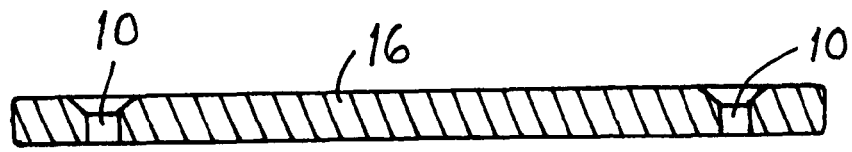
FIG. 11 is a longitudinal section of the plate according to the invention.

The positioning of the flat plates of this invention is preferred to be with their bottom face in substantially flush contact with the bone surface to which they are applied, and with a plurality of fasteners disposed therethrough to an enhanced secured position, wherein the head of the surgical fastener is tightened against the top face of the flat plate of this invention. This arrangement results in an enhanced secured relation between the flat plate of this invention and the underlying bone surface. FIG. 1 shows an example of plates with fasteners inserted through the openings into the bone. According to an advantageous embodiment the fastener opening 10 is conically widened on the top face of the plate so that it forms a countersink on the top face of the plate 15 to match with the head of the fastener, as shown by FIG. 11.

In addition to a simple plate 15 with a constant width and one or several fastener openings 10, the oriented, bioabsorbable plate of the invention can have such a design that the width of the plate in the area of the isthmus between two fastener openings is smaller than the width of plate around the fastener openings (or the width of the area into which additional fastening openings can be drilled). A special advantage of such plates is that these plates can be deformed easily also in the flat plane of the plate in addition to bending and torsional deformations, which are typical for constant width plates. Also the thickness of flat plates of this invention can be different in different parts of the plate.

When fully inserted, the head of the bone fixation screw or other fastener may be mainly or substantially contained at or below the top face of the plate of the invention thereby complementing the low-profile configuration of the osteosynthesis plate. The bone screw or other fastener may be made from the same or different biocompatible and bioabsorbable material as the osteosynthesis plate, thereby providing a fully bioresorbable bone stabilization device system.

Referring to prior art, like U.S. Pat. No. 6,221,075, there are available a plurality of geometries or configurations of osteosynthesis plates which configurations can be applied in manufacturing of oriented plates of the present invention. Typical configurations of such plates are e.g. I-plates (straight plates), L-plates, T-plates, Y-plates, X-plates, H-plates, square-plates, triangle plates, etc. Flat plates of this invention can also be bent during manufacturing in the flat plane of the plate and/or in any other plane to achieve any desired 2- or 3-dimensional geometry of the plate.

The plates according to this invention can be also mesh-plates e.g. with a plurality of smaller holes for fastener fixation and optional bigger holes to facilitate tissue healing through the plate and to reduce the mass of the plate. The plate material has relatively high strength around the holes due to the orientation patterns discussed above.

It will be appreciated that the examples set forth above are meant to be illustrative of the varieties of osteosynthesis plate shapes which may be constructed according to the present invention. It will further be appreciated that these osteosynthesis plates may be constructed of any of the materials previously discussed, or may be constructed from other suitable bioabsorbable materials. As before, it is preferred that any of the above osteosynthesis plates be constructed of a bioabsorbable (bioresorbable) material. As before, the bioabsorbable material may be combined in a bone stabilization device with bioabsorbable surgical fasteners, such as bone screws.

In addition, it will be appreciated that any of the above osteosynthesis plates may be constructed to include means disposed upon the elongated section to permit the formation of additional fastener openings therethrough during a surgical procedure, as provided e.g. in EP 0 449 867 B1. Further, all of the above-mentioned osteosynthesis plates are intended to be of a low-profile configuration, constructed in a flat configuration.

The osteosynthesis plates of the present invention can be manufactured of thermoplastic bioabsorbable (bioresorbable or biodegradable) polymers, copolymers, polymer alloys, or composites e.g. of poly-α-hydroxy acids and other aliphatic bioabsorbable polyesters, polyanhydrides, polyorthoesters, polyorganophosphatzenes, tyrosine polycarbonates and other bioabsorbable polymers disclosed in numerous publications, e.g. in S. Vainionpää et al., Prog. Polym. Sci., 14 (1989) 679-716, FI Pat. No. 952884, FI Pat. No. 955547 and WO-90/04982, EP 0449867 B1, U.S. Pat. No. 5,569,250, S. I. Ertel et al., J. Biomed. Mater. Res., 29 (1995) 1337-1348 as well as in the reference publications mentioned in the aforementioned publications.

Implants in accordance with this invention can be manufactured of bioabsorbable polymers by using one polymer or a polymer alloy. The implants can also be reinforced by reinforcing the material by fibres manufactured of a resorbable polymer or of a polymer alloy, or with biodegradable ceramic fibres, such as β-tricalciumphosphate fibres, bioactive glass fibres or CaM fibres (cf. e.g. EP146398). Ceramic powders can also be used as additives (fillers) in implants to promote new bone formation.

Implants according to the invention can also contain layered parts comprising e.g. (a) a flexible outer layer as a surface layer improving the toughness and/or operating as the hydrolysis barrier and (b) a stiff inner layer.

It is natural that the materials and implants of the invention can also contain various biocompatible additives for facilitating the processability of the material (e.g. stabilizers, antioxidants or plasticizers) or for changing its properties (e.g. plasticizers or ceramic powder materials or biostable fibres, such as carbon) or for facilitating its treatment (e.g. colorants).

According to one advantageous embodiment the implant of the invention contains some other bioactive additive(s), such as antibiotic(s) or other drug(s), chemotherapeutic agents, agents activating healing of wounds, growth factor(s), bone morphogenic protein(s), anticoagulant (such as heparin) etc. Such bioactive implants are particularly advantageous in clinical use, because they have, in addition to their mechanical effect, also biochemical, medical and other effects to facilitate tissue healing and/or regeneration.

A typical manufacturing procedure to make plates of the present invention is as follows:

First the polymer raw material (+optional additives and/or filler(s) and/or reinforcing fibers) in the form of a powder, flakes, pellets or granulate, etc., will be melted (melt molded) with a continuous process, like extrusion, or with a non-continuous process, like injection molding or compression molding. The melted material will be cooled so that it solidifies to an amorphous or partially crystalline (crystallinity typically 5-50%) preform, like a cylindrical rod or bar, a flat balk with a rectangular cross-section, a plate or a sheet stock, etc. Cooling can be done inside a special mold in injection molding and in compression molding techniques. In extrusion, the preform will be formed from material melt in a die and the preform will be led onto a special cooling belt or into a cooling solution to make a solid continuous preform. The preform can be cooled to room temperature and heated again to a temperature above Tg of the material for spiral orientation. The preform can also be cooled after melt molding to a temperature above Tg of the material and the spiral orientation can be done directly thereafter, with the help of additional heating if necessary to keep the preform above Tg.

The spiral orientation will be done by turning the other end of a longitudinal preform in relation to its other end around preform's long axis, at a temperature above Tg of the material (but below Tm, if any), in such a way that the preform material turns around the long axis of preform to a spiral orientation gradient, where the angle of helix (and the degree of orientation) is biggest at the surface of the preform and smallest (almost zero) in the core of the preform.

The turning of the preform can be done with a non-continuous, semicontinuous or continuous process by (a) keeping the other end of the preform in a non-turning position and turning the other end of the preform (see FIG. 2) or (b) by turning the both ends of the preform into opposite directions.

Figure 2A:
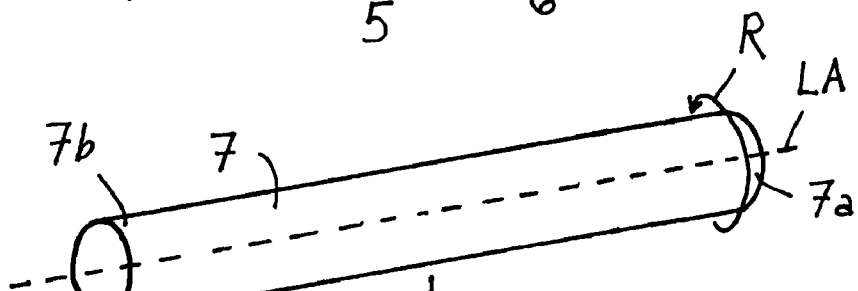
FIG. 2A shows a longitudinal, cylindrical, non-oriented or uniaxially oriented (drawn) preform.
Figure 2B:
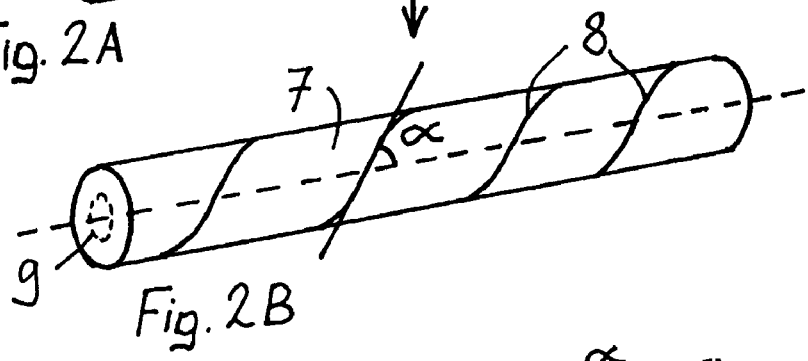
FIG. 2B shows schematically the preform of FIG. 2A after turning (twisting) it in the solid state around its long axis.
Figure 2C:
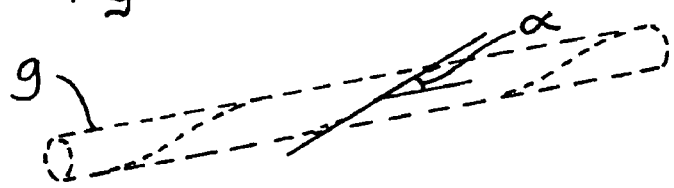
FIG. 2C shows schematically the spiral orientation inside of the preform of FIG. 2B, FIGS. 3A-3J show schematically the compression of a spiral oriented preform to a plate-like billet.

In FIG. 2A is shown schematically how the other end 7a of a cylindrical preform 7 is turned in relation to the other end 7b around the long axis LA of the preform 7 in the direction shown by the arrow R. FIG. 2B shows schematically the spiral orientation mode on the surface of the preform where orientation flow lines 8 have been formed. Flow lines can form on the surface of the preform during turning, if on the surface are irregularities, like roughness. Flow lines may also be seen after chemical and/or physical etching of the surface. The spiral orientation can be characterized by the angle of helix, alpha, which has its maximum value (strongest orientation) at the surface of the preform 7 (see FIG. 2B). The character of the spiral orientation gradient of the preform is illustrated schematically by FIG. 2C, describing the spiral orientation inside of the preform 7 on the layer 9 (ca. halfway between the surface and inner core of the preform 7). Spiral orientation is here weaker than on the surface of the preform and the angle of helix, alpha', is here substantially smaller than the angle of helix, alpha, on the surface of the preform 7.

Because the spiral orientation (and the angle of helix) changes continuously from the maximum value on the surface of the preform 7 to the minimum value in its inner core, a spiral orientation gradient is achieved by turning of the preform 7. This transforms a brittle and weak preform effectively to a tough and ductile one.

According to an advantageous embodiment, the cylindrical preform can be drawn longitudinally (uniaxially) along the long axis LA before spiral orientation. The longitudinal drawing in the solid state at a temperature T>Tg (and below Tm, if any) will create into the preform longitudinal orientation, which toughens the preform, which makes then the spiral orientation of the preform more easy. The inner core of such a spiral oriented preform is oriented almost uniaxially (in the longitudinal direction) giving for the preform good mechanical behaviour under tensile load. By combining uniaxial drawing and spiral orientation with different drawing ratio and spiral orientation ratio combinations, it is possible to change effectively the orientation gradient and by this way different mechanical properties of the final oriented plate-like billet.

It is also possible to draw the preform uniaxially and turn it to the multiaxial spiral orientation simultaneously or make spiral orientation first and draw the preform uniaxially thereafter.

The spiral orientation of the cylindrical preform can be done with a continuous process by drawing the preform at a temperature T>Tg (but below Tm, if any) through a cylindrical heated die and by turning the die around its axis so that the preform turns around its axis when coming out of the die. Longitudinal orientation of the preform by drawing can be done also simultaneously.

In another continuous process the preform is drawn also at a temperature T>Tg, (but below Tm, if any) through a heated, static die, but the drawing machine, like drawing caterpillars, is turned around the long axis of the preform.

The heating of the preform above Tg is not necessary if the preform is oriented relatively soon after its formation. In a continuous/semicontinuous process of this kind, the preform is drawn and spirally oriented also at a temperature T>Tg (but below Tm, if any) during the continuous melt flow process, such as extrusion, by drawing and twisting one end of the preform after the die of extruder by presence of additional heating unit, and then pressing it into a form of a flat strip by using heated roller or cooled roller in combination with external heating unit, and cooled down afterwards. By using this method the perform or flat strip has to be cut after certain periods of time.

In one semicontinuous process of spiral orientation, the end part of a long, unoriented preform is first heated to a temperature T>Tg (and below Tm, if any), optionally drawn uniaxially thereafter and turned from the tip of the end part around the long axis of the preform keeping the non-heated long part of the preform without turning. The long unoriented preform can typically be several meters long (or even tens of meters or hundreds of meters long if it is e.g. coiled on a big roll or reel). The heated and orientable (turnable) part of preform is typically from some centimeters to 40-50 cm or even longer.

Figure 3A:
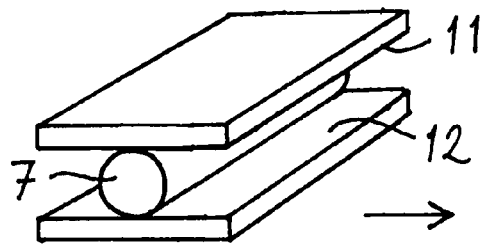
Figure 3B:
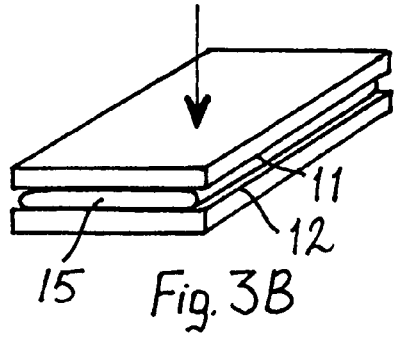

After the spiral orientation, and optional uniaxial orientation before, during or after spiral orientation, the oriented preform, or the heated, oriented part of a long preform, will be compressed into the form of a plate-like billet at a temperature T>Tg (but below Tm, if any) in a compression mold, as is seen schematically in FIG. 3. FIG. 3A shows a cylindrical, spiral oriented preform 7 (like e.g. that of FIG. 2B) as located into a compression mold between opposite flat mold surfaces 11 and 12. When the mold is closed by moving the mold surfaces 11 and 12 towards each other, the cylindrical preform 10 is transformed (flattened) to a plate-like billet 15. When the compression is done at a temperature T>Tg of the material (and T<Tm in the case of a partially crystalline preform) and the mold and the final plate billet is cooled to a temperature below Tg before opening of the mold, the orientation is retained in the final one-piece plate billet as a diagonal orientation gradient.

Figure 3C:
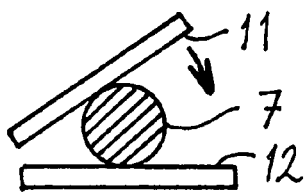
Figure 3D:
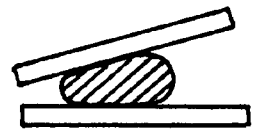
Figure 3E:
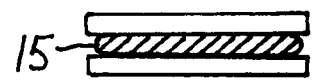

FIGS. 3C, 3D and 3E show examples of gradual compression where one side of the preform 7 is compressed first more and the compression proceeds to the other side, in a direction perpendicular to the reference axis (long axis LA), until a plate of constant thickness is obtained. The mold surfaces 11, 12 are first at an angle which will close and become zero as the compression proceeds and is concluded. This procedure will result in a piece where the orientation pattern is asymmetrical with reference to the central reference axis (long axis LA) due to the shifting of the material tranversely with respect of said axis from one side to the other side.

Figure 3F:
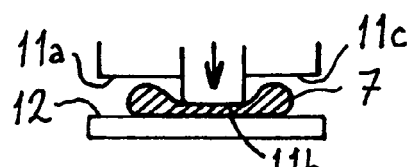
Figure 3G:
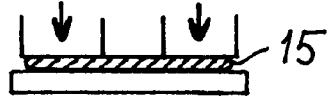

FIGS. 3F and 3G show examples of a compression procedure where the compression is performed in zones of the preform. First a central zone extending in the direction of long axis LA is compressed, and thereafter the adjacent zones on both sides of it. One of the mold halves consists of several flat mold surfaces 11a, 11b, 11c movable independently of each other in the compression direction.

The plate-like billet can be made from the cylindrical preform 7 (or from the heated part of a long preform) also with other methods. E.g. the spiral oriented cylindrical preform can be forced through a rectangular flat die by pushing the preform mechanically with a piston through the die (ram extrusion) or by pushing the billet through the die with hydrostatic pressure (see e.g. N. Inoue, in Hydrostatic Extrusion, N. Inoue and M. Nishihara (eds.), Elsevier Applied Science Publishers, Barbing, England, 1985, p. 333-362) to change the preform to a plate-like billet 15, which has a diagonal orientation gradient.

It is also possible to change the spiral oriented preform 7 to a plate-like billet 15 by shearing the (cylindrical) preform between two flat plates which glide in relation to each others and approach each other at the same time.

Figure 3H:
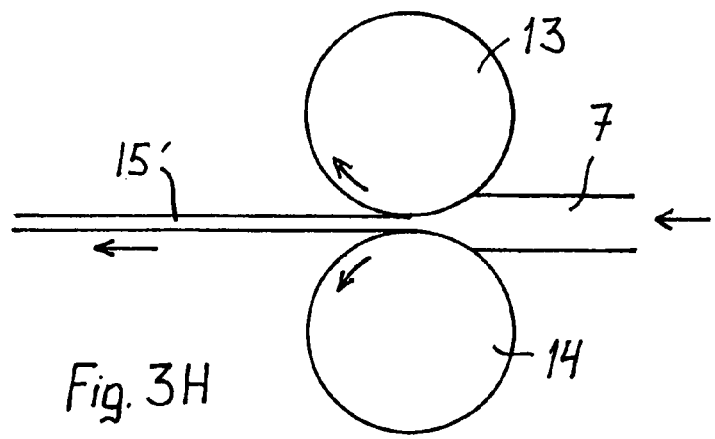

The deformation can be done also by rolling the spiral oriented preform 7 between rollers, which flatten the preform to the desired plate thickness, using e.g. the roller construction whose principle has been described in U.S. Pat. No. 6,221,075, in its FIGS. 10 A and B. FIG. 3H shows an example of such a continuous compression where an elongated spirally oriented preform 7 is compressed by a roller 13 so that the compression proceeds in the direction of long axis LA. The preform is fed in its longitudinal direction into a gap between the roller and a counter surface, which may be another rotating roller 14. The result is a continuous strip 15' which can be cut to individual plates. After the roller and the counter surface, for example rollers 13, 14, there is a zone of cooling and possible additional compression rollers downstream of them so that the strip can retain its flattened shape.

It is natural that different deformation methods can be combined to each others. E.g. hydrostatic deformation can be combined to die drawing or rolling can be combined to drawing, e.g. by using two pairs of rollers after each other, which rollers have different rolling speeds, etc.

The preform and/or compression plates or die, or rolls can be heated to the desired deformation temperature with electrical heating, with infrared radiation or with a suitable heating medium, like a gas or heating liquid. The heating can be done also with microwaves or ultrasonically to accelerate the heating of the preform.

FIGS. 3I and 3J show an embodiment where the plate to be produced does not extend along a straight plane, but is curved. This structure is designed for the fracture fixation of small bones so that the plate shape would be already in approximate conformity with the contour of these bones. The main plane of the plate is curved in cross-section taken perpendicularly to the long axis LA. The curved shape of the plate-like billet 15 is obtained by correspondingly curved mold surfaces 11, 12 in compression molding of the preform 7.

The surface orientation is described in the schematic FIG. 4. FIG. 4A shows the spiral oriented cylindrical preform 7 with the spiral lines 8, characterizing orientation on its surface. After compression molding of the preform 7 to a plate-like billet 15 the spiral orientation is retained in the compressed plate-like billet as diagonal orientation gradient. The diagonal (oblique), uniaxially oriented surface layer is shown schematically with lines 8' in FIG. 4B. It should be noted that FIGS. 4A and 4B are meant to be illustrative of the general principle underlying the invention and not exact representations of the orientation patterns.

Figure 5:
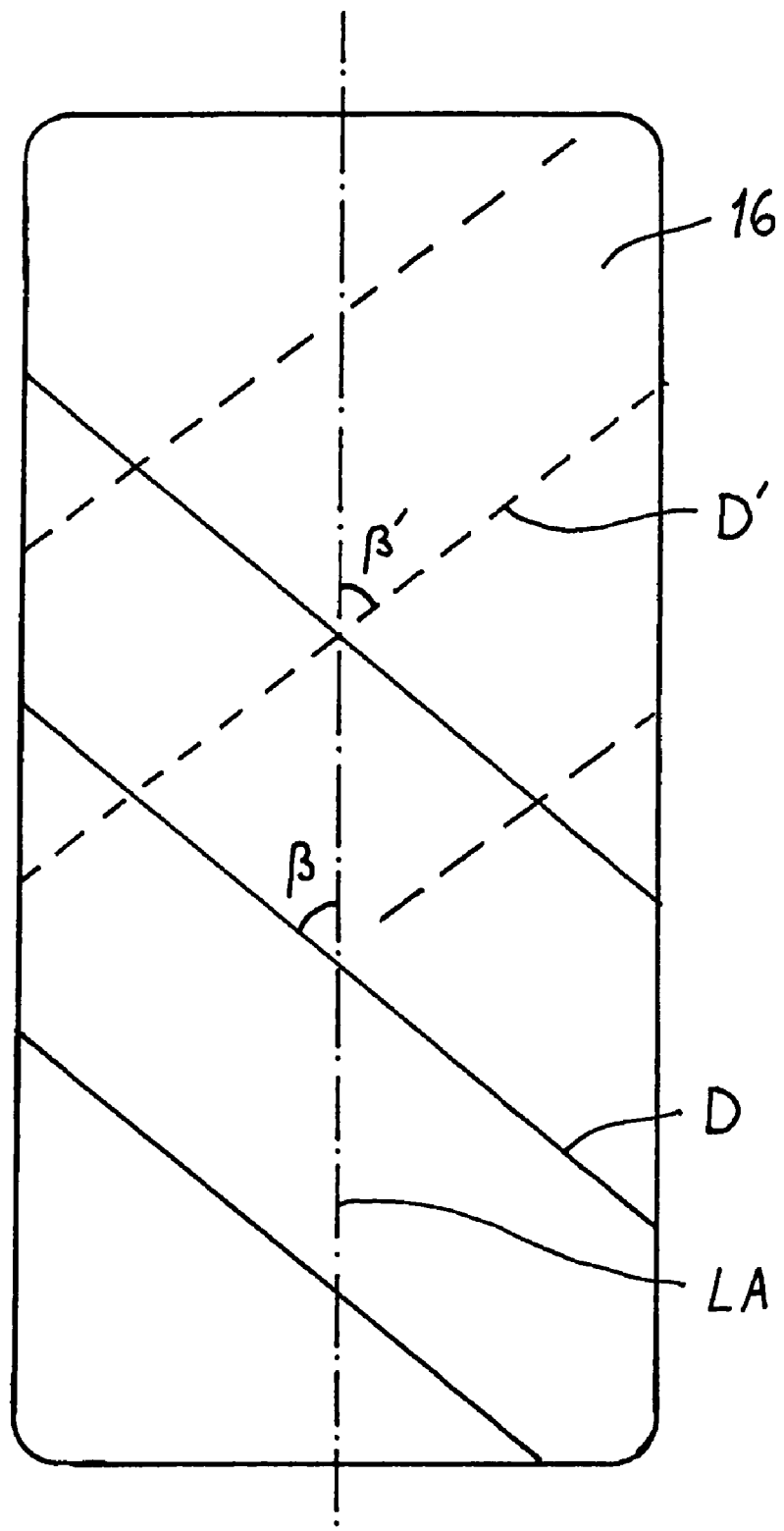
FIG. 5 shows schematically the diagonal orientation on the first (upper) flat surface and on the second (lower) flat surface of a plate according to the invention.

FIG. 5 shows schematically the upper flat surface (first surface) of a diagonally oriented plate 16 with diagonal uniaxial orientation on this surface. The orientation direction D (solid lines) makes an angle beta with the direction of long axis LA of the plate 16. On the lower flat surface (second surface; not seen here) of the plate 16 the direction of diagonal uniaxial orientation (D', dashed lines) makes an angle beta' with the direction of the long axis (LA) of the plate 16. In an imaginary plane in the interior of the plate midway between the upper and lower surfaces the orientation follows approximately the direction of the long axis LA, as a result of uniaxial drawing.

FIGS. 6A and 6B describe schematically the character of orientation gradient as examined against the direction of the flat surface of a plate 16 according to the invention. The diagonal orientation on the flat surface (first surface) of the plate 16 is described with solid lines. The diagonal orientation in a layer below the plate surface is described with dashed lines and the diagonal orientation in a still deeper layer, near the core of the plate is described with dotted lines. Because of clarity, dashed and dotted lines are drawn only in a part of the plate 16 although the orientation gradient, of course, comprises the whole plate.

The solid, dashed and dotted lines of FIGS. 6A and 6B describe the orientation gradient so that the direction of diagonal orientation changes from strongly oblique on the plate surface (first surface) to less oblique in inner parts of upper side of the plate 16. On the lower side of the core of the plate the orientation gradient turns into opposite direction when compared to the upper side of the core. Because on the lower side of core of the plate 16 is similar type of orientation gradient structure as on the upper side, however with the opposite direction of obliquity, the diagonal orientation gradient of the plate forms a strong and tough multiaxially oriented structure with strong diagonal orientations (in opposite directions) on outer surfaces, which change through weaker diagonal orientations to almost longitudinal orientation in the middle of the plate. Such an orientation gradient structure carries effectively different types of mechanical loads and prevents effectively splitting of the plate, even when fixed with fixation devices on the surface of bone.

However, it should be noted that, depending on the method of forming the plate, the orientation is not necessarily constant in the same imaginary plane. For example flattening of a rod-shaped preform 7 may result in a steeper orientation (larger angle beta 2) at the edges than in the middle of the plate 16 (beta 1), as shown in FIG. 6A. However, when the orientation is compared perpendicularly to the plane of the plate within a given zone, for example in a central zone along the long axis, the pattern of gradually changing orientation (angle beta) exists. FIG. 6A shows the result of the flattening step of FIGS. 3A and 3B, where the compressing surfaces 11 and 12 are continuously parallel to each other when they are closed. FIG. 6B depicts the case where the surfaces 11 and 12 form a closing gap or the acute angle between them decreases when they are closed (FIGS. 3C-3E). This results in a plate 16 where the angle beta gradually increases from one edge (angle beta 1) to the other one (angle beta 2), in the opening direction of the gap.

The cross-section of the preform 7, which in this invention is transformed finally to a plate 16 of the invention, is typically cylindrical. However, other forms of the preform are also possible. FIGS. 7A-7F show some advantageous cross-sections of preforms 7 of the invention. The cross-section of a typical cylindrical preform 7 is seen in FIG. 7A. The diameter of the preform is typically from 2 to 20 mm. FIG. 7B shows a flat (ellipsoidal) cross-section of a preform 7.

Figure 8A:
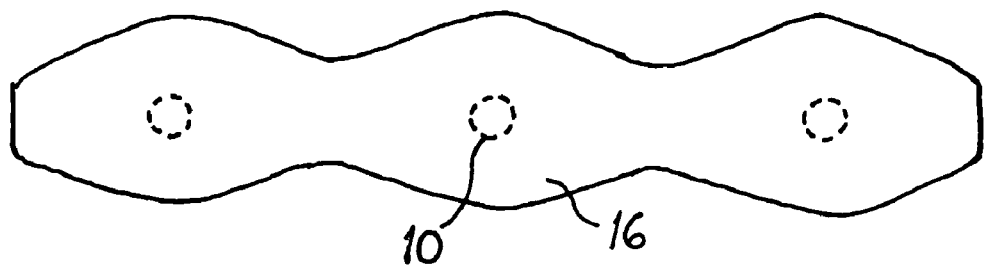
FIG. 8A shows schematically the form of a plate of the invention, which plate is made of a non-cylindrical preform.

FIG. 7C shows a quadrangular and FIG. 7D a square cross-section of a preform. FIG. 7E shows a triangular cross-section of a preform 7. The preform 7 can be also cannulated (a hole is made through the preform) as is seen in FIG. 7 F, i.e. tubular. When non-cylindrical preforms 7, like those of FIGS. 7B-7F are spiral oriented and flattened to plate-like billets 15, billets with different geometries are achieved. E.g. when a preform 7 with an ellipsoidal cross-section (like in FIG. 7B) or quadrangular cross-section (like in FIG. 7C) is spiral oriented and flattened to a plate-like billet, a plate with varying width can be achieved. Such a plate 16 is seen schematically in FIG. 8A. Fastener holes or openings 10 can be formed in the wider areas, as shown by dashed lines.

In another continuous/semicontinuous process two or more preforms are drawn and twisted in a way they will twist around each other forming double, triple, etc. helix structure and these performs are later pressed into form of plates.

In one variation, two (or several) preforms are drawn and twisted together to a double or multiple helix structure so loosely that they form an assembly where openings remain between single preforms. In the subsequent compression step in the mold, single preforms can be kept separate at the openings by pins. Thus, fastener holes can be formed simultaneously with the compression step in the plate. The holes are defined by the edges of the original preform material. Thus, no material needs be removed for forming the holes in the plate. According to another method, pins are inserted between single preforms before twisting them to a double or multiple helix structure to define the openings for the subsequent compression step.

The proper adhesion between adjacent preforms of multiple helix structure may be achieved by using ultrasonic welding/molding, heat treatment, or an adhesive.

Figure 8B:
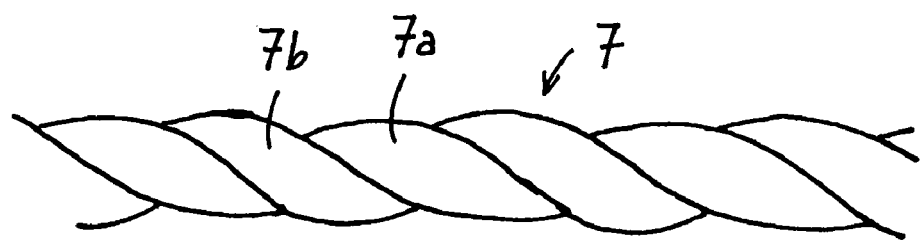
FIGS. 8B-C show the formation of a double-helix preform to a plate-like billet.
Figure 8C:
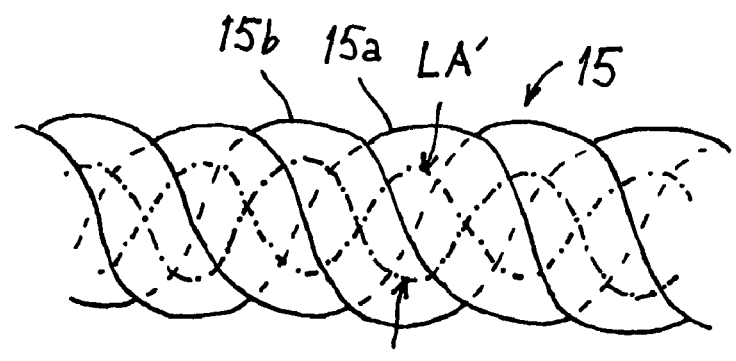
Figure 10A:
FIG. 10 shows schematically how a Y-plate (FIGS. 10A-10C) and an X-plate (FIGS. 10D-10F) can be made of the plate of the invention with partial splitting and bending of the plate (or preform of the plate)
Figure 10B:
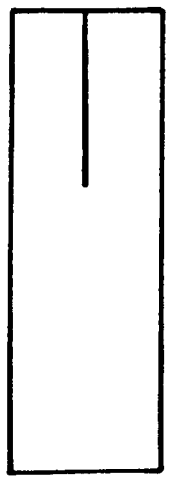
Figure 10C:
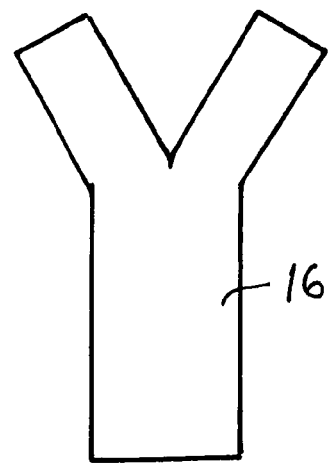
Figure 10D:
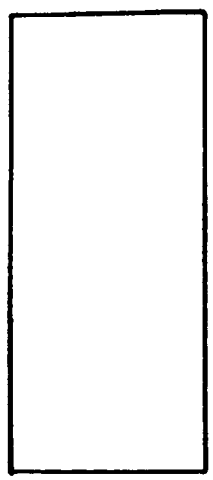
Figure 10E:
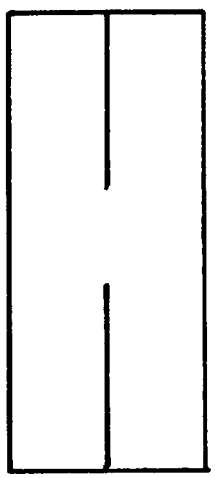
Figure 10F:
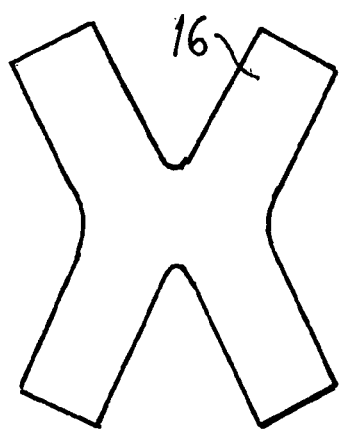

FIG. 8B is a top plan view of a preform 7 which is made up of two separate strands 7a, 7b which are twisted together so that they form a double helix twisting around a long axis LA. Both strands 7a, 7b have spiral orientation of their own as a result of twisting. In addition, they may have been spirally oriented, separately before twisting. Both strands are also preferably oriented uniaxially before twisting them together. FIG. 8C shows the structure after the compression stage. The double helix has been flattened to a plate-like billet 15 where wider and narrower areas alternate. The final plate will thus be formed of two plate portions 15a, 15b each originating in a single strand 7a, 7b and mutually interlocked mechanically. Each plate portion has a diagonal orientation gradient in relation to its own long axis LA' denoted with broken lines, as the result of the original spiral orientation, and the plate has a combined orientation gradient in areas where the plate portions overlap. The plate portions can be attached together permanently by ultrasonic welding or by a low-melting glue or any other suitable method, such as heat treatment to a softening point under compression. Wider areas can be used for forming fastener holes. More than two strands can be drawn and twisted together to a multiple-helix preform, and the compression to a plate form takes place analogically.

When a cannulated preform (as is described e.g. in FIG. 7F) is spiral oriented, a solid cylindrical mandrel, with a low-friction surface (like Teflon coating), must be placed into the hole inside of the preform, to prevent its collapse during spiral orientation (turning or twisting).

FIGS. 9A-9C show schematically, how a spiral oriented, cannulated preform 7 of FIG. 9A can be cut open along its long axis, to form a cut preform 7', as is seen in FIG. 9B. Thereafter the cut preform can be opened totally by bending it open and compressing it to flatten it to a plate-like billet 15, which is seen in FIG. 9C. The spiral orientation on the inner surface of the cannulated preform 7, cut preform 7' and the diagonal orientation on the surface of the broad plate are given with dashed lines. A diagonal orientation gradient through the thickness of the plate exists in this embodiment as well, but the angle beta with respect to the long axis only decreases but does not approach zero and change to opposite. Such broad plates, as e.g. is seen in FIG. 9C can be used as fixation plates as such or they can be processed to mesh-plates, by making suitable perforations to them or suitable plates, like I-, Y-, X-, L-, etc. plates can be made of them with suitable mechanical machining or other cutting methods.

FIGS. 9D-9E show an alternative method of working the perform 7 of FIG. 9A to a flat plate-like billet 15. The cannulated prefrom 7 is not cut open, but it is compressed to a flat configuration so that the inner surfaces of the preform 7 meet. The result is a sort of layered plate where the layers are integrated at edges. In this plate there is a diagonal orientation gradient where the diagonal orientation runs in opposite direction on the opposite side of the plate. The inner walls of the preform 7 that come in contact on flattening the preform can be held together by a low melting glue and/or reinforcing elements can be used between them. For example a bundle of reinforcing fibers or a fabric can be placed inside the preform before compressing (flattening) it into the plate-like billet 15. In use, the plate can be internally fixed also by the effect of fasteners introduced through the holes of the plate.

Y-, X-, H- or other branched plates 16 can be done also from long, straight, diagonally oriented plates by splitting one or both plate ends in the plane perpendicular to the flat plane of the plate and bending the split parts outwards, as is seen schematically in FIG. 10. FIGS. 10A-C show, how a long straight plate is split from one end and formed to a Y-plate by bending the split parts outwards in the flat plane of the plate. FIGS. 10D-F show a similar process to make an X-plate.

Branched plates can be done also from spiral oriented preforms 7 by splitting one or both ends of preform and by bending the split parts outwards before or after plate compression.

Other shapes are also possible by shaping the spirally oriented preform. For example it can be bent at one or more angles, which results in similar angles in the plate, or it can be bent into a curved shape. For example plates in the shape of L can be formed by bending a portion of the spirally oriented preform at right angles before compression. The long axis (reference axis) forms one or more angles or is curved accordingly in the final plate. The bending can be done in a mold that corresponds to the desired shape.

Regardless of the deformation method, the purpose of the spiral orientation and compression is to transform the material to a state where it is substantially rigid, tough and substantially deformable at conditions of surgical operation.

Solid state deformation, to create oriented bioabsorbable fixation materials, has been described in several publications, like in U.S. Pat. No. 4,671,280, U.S. Pat. No. 4,968,317, U.S. Pat. No. 4,898,186, EP 0 321176 B1 and WO 97/11725, D. C. Tunc and B. Jadhav, in Progress in Biomedical Polymers, eds. C. G. Gebelein and R. L. Dunn, Plenum Press, New York 1992, p. 239-248, FI Pat. No 88111, FI Pat. No 98136 and U.S. Pat. No. 6,221,075. However, only in this invention we have found surprisingly, that when the rigid bioabsorbable (bioresorbable) fixation implant material, which cannot be deformed substantially without damage at temperatures below Tg of the material, is transformed to the state of diagonal orientation gradient, it is also changed to a material which is substantially rigid but can be deformed substantially at temperatures below Tg of the material to use it advantageously in bone fracture fixation.

The diagonal orientation gives for the plate-like billet excellent ductility and toughness so that it can be deformed at room temperature without breaking.

Following the spiral orientation step and flat billet compression steps, osteosynthesis plates can be formed from the diagonally oriented plate-like billets by machining or stamping the plate and the fastener opening(s) and the countersink(s). The compression of spiral oriented preform can also be done in a mold which forms the final plate with the final plate geometry, fastener opening(s) and optional countersink(s) in one step.

According to an advantageous embodiment of the invention the spiral oriented preform can be covered with a tube-like fibrous fabric ("stocking"). This can be a tube-like braid, textile, etc. which is slipped on to the preform before compressing it to the plate-like billet. The tube-like fibrous fabric can be knitted, weaved, twisted or manufactured with some other method of textile technology of bioabsorbable polymeric and/or biodegradable ceramic or bioactive glass fibers. By selecting in the proper way the fibers of the fabric, it is not damaged during compression, but forms a tight reinforcing and stiffening structure on the surface of the diagonally oriented plate-like billet.

Reinforcement can also be in a form of discontinuous fibres (bioactive glass, calcium phosphate ceramic fibres or biologically stabile fibres), which are compounded with matrix polymer during melt flow process, such as extrusion. If the discontinuous fibres (length above critical fibre length) are added into matrix polymer in the end of extrusion process and the billet is drawn by twisting one end of the billet after die, also the orientation of reinforcing fibres may be oriented similarly to polymer chains. After that the perform will be pressed into final form.

The final step of the method of the present invention may involve the finishing of the plates, to enhance a smooth surface and an aesthetic appearance of the article. This is accomplished by trimming with suitable trimming devices, such as knives or cutting blades, or may also be accomplished by an additional stamping step. Once the removal of surface irregularities has occurred, the substantially completed product may be subjected to cleaning with a suitable cleaning agent, like ethyl alcohol water mixture. Mechanical agitation and ultrasonic agitation can be used to facilitate the cleaning. In this step, the outer surface of the osteosynthesis plate can be cleaned of fingerprints, soils and oils resulting from contact with human hands and other surfaces, as well as impurities which may collect on the surface.

In the next step of the method of the present invention the plates are dried in high vacuum, optionally at an elevated temperature, packed into a plastic foil and/or aluminium foil pouch(es) which is (are) sealed. Another drying step and filling of the pouch with an inert gas (like nitrogen or argon gas) before heat sealing of the pouch, may also be carried out.

Finally the plates closed into the packages, are sterilized, e.g. with γ-radiation, using a standard dose of radiation (e.g. 2.5-3.5 MRad). If gas sterilization will be used (like ethylene oxide), the plates must be sterilized before closing the package.

It is natural that the above-mentioned steps of manufacturing an osteosynthesis plate of the present invention may further include additional steps, such as for quality control purposes. These additional steps may include quality control testings during or between the various steps, as well as final product inspection including chemical and/or physical testing and characterization steps and other quality control testings.

The invention also encompasses half-fabricates in the form of spirally oriented preforms, which may have been longitudinally oriented or not. These half-fabricates can be in any shape discussed above before compression or working in any other way to flat plate-like configuration. They can be stored and dispatched below Tg of the material, for example at room temperature, and reheated above the Tg in connection with final working step.

The method for enhancing a substantially secured relation between a plurality of adjacent bone portions according to the present invention is described next. The first step of this method includes providing a sterile, low-profile, diagonally oriented biocompatible osteosynthesis plate of the invention. This is achieved by opening the plate package in an operation room by an operation table and supplying the sterile plate to the surgeon. Depending on the surface topography of the bone to be fixed the surgeon then shapes (deforms), if necessary, the osteosynthesis plate to a first desired configuration by hands or with special manipulation instrument(s). The surgeon can then test the result of shaping conveniently by pressing the plate gently against the bone to be fixed and if the first desired configuration is not sufficient for completing the surgical requirements, the surgeon can reshape the osteosynthesis plate to a second desired configuration.

In addition, it will be appreciated that the method of the present invention further includes the capability for repetitively reshaping, at constant operation room temperature, the osteosynthesis plate to successive desired configurations and ceasing reshaping the osteosynthesis plate when a desired final configuration of the osteosynthesis plate has been achieved.

The osteosynthesis plate is then positioned upon a plurality of adjacent bone portions. A plurality of surgical screws or other fasteners are then provided for enhancing a fixed relation between the osteosynthesis plate and at least one adjacent bone portion. A plurality of surgical screws or other fasteners are then positioned within a plurality of fastener openings located upon the osteosynthesis plate. The plurality of surgical screws or other fasteners are then secured to the adjacent bone portions, thereby engaging the low-profile biocompatible osteosynthesis plate with each bone portion.

This method may further include the additional steps of creating at least one additional fastener opening through the osteosynthesis plate at a location adjacent to at least one bone portion, positioning an additional surgical fastener (like a screw or other fastener) within each additional fastener opening, and substantially securing each additional surgical fastener into each bone portion thereby enhancing an engagement of the osteosynthesis plate with each bone portion as was described e.g. in EP 0 449 867 B1. This method may also include the step of engaging the osteosynthesis plate with at least one adjacent osteosynthesis plate.

Alternatively, the method for enhancing a substantially secure relationship between a plurality of adjacent bone portions is similar to that described above, but the osteosynthesis plate is secured by means of an adhesive. In this regard, after the osteosynthesis plate is formed in the manner described above, the surgeon places an adhesive between the bone portions to be secured and the osteosynthesis plate. The surgeon then brings the osteosynthesis plate into contact with the bone portions thereby securing the osteosynthesis plate to the bone portions.

The principles of the present invention described broadly above will now be described with reference to the following specific example, without intending to restrict the scope of the present invention.

Example 1

Commercially available medical grade PLGA 85L/15G polymer granulate [Boehringer Ingelheim, Germany; polymer having inherent viscosity 5.5 dl/g, when measured at 25° C. as dissolved in chloroform (20 mg/20 ml)] was melt extruded with a custom made 20 mm twin screw extruder to an elongated cylindrical rod (diameter≈6.1 mm) which was cooled to room temperature. The inherent viscosity of such a melt extruded preform was about 3.5 dl/g. The melt extruded preform was fastened at one end to a moving part of a custom made plate manufacturing device. Another (not moving) fastening point was 60 mm apart from the fastened end of the preform. The preform between the fastening points was heated with hot air to about 80° C. The moving part was pulled 88 mm along the longitudinal axis of the preform, thus the preform was longitudinally stretched from 60 mm to 148 mm yielding a draw ratio of 2.5. The moving part was then rotated 4 rounds around the longitudinal axis of the preform, which was in the stretched state, in order to create spiral orientation. These orientation procedures took place in a mold, between heated flat mold surfaces, which were at a distance of about 50 mm from each others (one above and another below the preform). The preform did not touch the mold surfaces during the drawing and spiral orientation steps. Right after the spiral orientation the mold was closed and the longitudinally and spirally oriented cylindrical preform was compression molded to a flat plate-like billet with the thickness of ca. 1.1 mm. The mold temperature during compression was 90° C. The width of the mold cavity was 8 mm and length of the mold cavity was 80 mm. Both ends of the mold cavity were open, which enabled the locking of the preform to the mounting points at both ends of the mold throughout the compression molding cycle. This impeded the relaxation of the orientation during the compression molding cycle. After about 30 seconds of compression with a force of about 10 kN the mold was cooled down to 20° C. within 30 seconds and the mold was opened. The plate with the orientation gradient (diagonal orientation on surfaces changing progressively to the longitudinal orientation in the core of the plate) was removed from the mold and the excess material, which had been outside the mold was cut off from the ends of the plate. The plate dimensions were about 80×8×1.1 mm. To test the malleability of the plate it was bent manually, dry, at room temperature between fingers to an angle of 180° and back. There were no signs of damage in the plate after this bending procedure. Also slow repeatable bending did not damage the plate. The plate kept well its deformed state. The test was repeated with 3 plates with identical results. This kind of malleability is excellent for use in operating theater to enable the manual adjustment of the plate ("as-bendable plate" or "RT-bendable plate") to fit well on bone surfaces, without heating the plate. In addition to manual malleability test, shear strength of oriented plates was measured, according to the publication P. Törmälä et al., J. Biomed. Mater. Res. 25 (1991) 1-21, at room temperature for dry samples. The shear strength of the plate in 90° angle to the longitudinal axis of the plate was 65 MPa.

Non-oriented reference plates were done with compression molding from the similar melt extruded rods with the above method, excluding the rod stretching and spiral orientation steps. The non-oriented, compression molded plates (with dimensions 80×8×1.1 mm) were bent manually, between fingers, dry at room temperature, in the same way as oriented plates. All tested plates (3 samples) broke in similar bending tests carried out for the plates according to the invention.

So it was shown, that non-oriented plates were not as-bendable, but brittle and weaker compared with the plates of the invention.

Example 2

Figure 12:
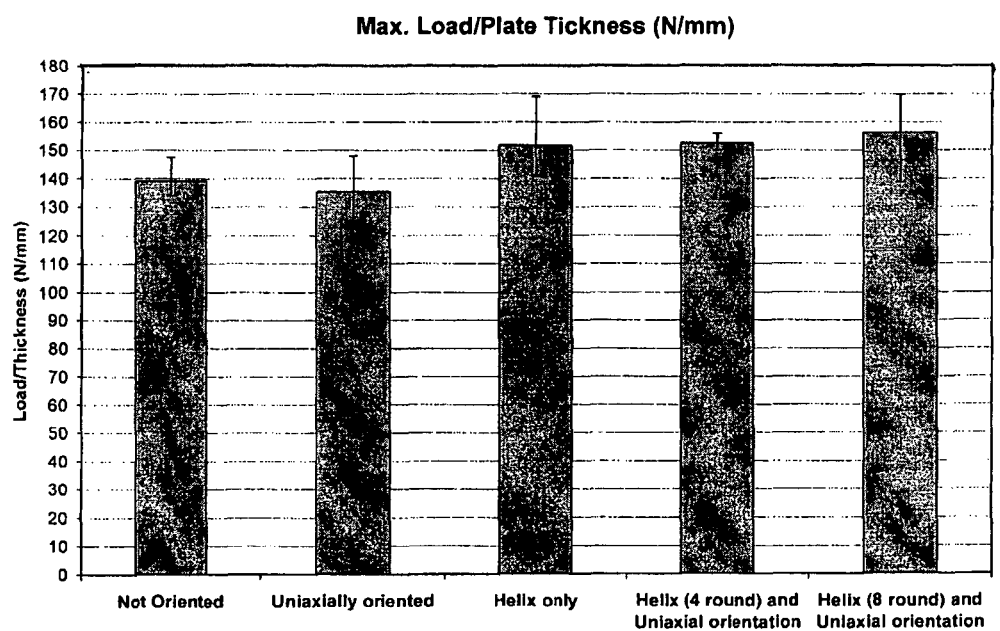
FIG. 12 shows the results of hole tearing tests carried our with the plates of the invention.

Hole Tear Test
Equipment:
INSTRON 4411 (tensile testing machine at TTY/Institute of Biomaterials)
Crosshead speed: 10 mm/min
Cell: 5 kN
Gauge length 50 mm
Hole diameter in plate: 0.7 mm
Metal string was used as a material to tear the hole Plates made from the same raw material by the same methods as in Example 1 were tested for the strength of the hole that is near the end of the plate. The hole was torn in the direction of long axis to the end edge with a metal string inserted through the hole. Maximum load/plate thickness was used as a test parameter. The results are summarized in FIG. 12. It can be seen that both helical orientation and helical orientation combined with uniaxial orientation increase the hole tearing strength compared with non-oriented and uniaxially oriented samples. Increase in the number of rounds per unit length in the helical orientation will also increase the tearing strength.

Surgical Methods of Using the Plate

As a summary, a method for securing a plurality of bone portions using an osteosynthesis plate with the oblique orientation gradient according to the invention comprises forming said osteosynthesis plate, including:
  (a) providing a material that is substantially rigid and substantially deformable and dimensionally stable at a first thermochemical state;
  (b) forming said material into said osteosynthesis plate;
  (c) securing said osteosynthesis plate to a plurality of bone portions.

According to one embodiment, the method for securing a plurality of bone portions comprises the steps of:
  providing an osteosynthesis plate having an oblique orientation gradient and being operable to be placed in a substantially secured relation with respect to the plurality of bone portions, said plate being composed of a material that is substantially rigid and dimensionally stable and substantially deformable at a first thermochemical state, said osteosynthesis plate including an elongated section having first and second surfaces;
  deforming said osteosynthesis plate at said first thermochemical state;

securing said osteosynthesis plate to the plurality of bone portions; and leaving the said osteosynthesis plate secured to the plurality of bone portions to allow absorption after fracture healing.

A method for securing a plurality of bone portions according to the afore-mentioned embodiment may further comprise the additional step of forming at least one opening between said first and second surfaces of said osteosynthesis plate after formation of said osteosynthesis plate.

In a method for securing a plurality of bone portions according to the afore-mentioned embodiment, said osteosynthesis plate is formed in a first configuration, and said step of deforming said osteosynthesis plate comprises the changing the shape of said osteosynthesis plate from said first configuration to a second configuration when said osteosynthesis plate is in a first thermochemical state.

In a method for securing a plurality of bone portions according to the afore-mentioned embodiment, said step of deforming said osteosynthesis plate comprises the steps of:
(a) changing the shape of said osteosynthesis plate while at said first thermochemical state;
(b) repeating step (a) until a desired configuration of said osteosynthesis plate has been obtained.

According to another embodiment, the method for securing a plurality of bone portions comprises the steps of:
providing an osteosynthesis plate with an oblique orientation gradient, said osteosynthesis plate being operable to be placed in a substantially secured relation with respect to the plurality of bone portions, said osteosynthesis plate including an elongated section having first and second surfaces, said osteosynthesis plate being formed from a material that is substantially rigid and substantially deformable and dimensionally stable when at said first thermochemical state;
forming at least one opening between said first and second surfaces of said osteosynthesis plate;
securing said osteosynthesis plate to the plurality of bone portions; and
leaving said osteosynthesis plate secured to the plurality of bone portions to allow bioabsorption after the plurality of bone portions have consolidated (ossified) together.

In a method for securing a plurality of bone portions according to said other embodiment, said material is deformable along three mutually perpendicular axes.

We claim:

1. A bioabsorbable surgical osteosynthesis plate, operable to be secured by at least one fastener through at least one fastener opening formed in the plate to a bone, said osteosynthesis plate having a first surface and a second surface and a thickness extending between the first surface and the second surface, the plate further comprising a main plane extending parallelly to the first surface and the second surface, the plate being formed to one piece from a spirally oriented preform of a material that is substantially rigid and substantially deformable and dimensionally stable at a first thermochemical state such that the plate is deformable to a deformed state where the plate maintains the deformed state, said material of the plate being oriented parallel to the main plane of the plate so that the plate comprises a continuous gradient of diagonal orientation of the material throughout the thickness of the plate, wherein polymer molecules or segments of polymer molecules are aligned in directions of the diagonal orientation in said material as a result of solid state deformation of the material, said orientation being diagonal in relation to the direction of a reference axis of the plate, wherein the first surface has a diagonal orientation and the second surface has a diagonal orientation such that the diagonal orientation of the first surface and the diagonal orientation of the second surface are in different directions.

2. The surgical osteosynthesis plate according to claim 1, wherein the obliquity of the orientation of the plate in relation to the direction of the reference axis is smaller inside of the plate than on the first and/or second surface of the plate.

3. The surgical osteosynthesis plate according to claim 1, wherein said plate has an elongated shape or section, the reference axis being the long axis of the elongated shape or section.

4. The surgical osteosynthesis plate according to claim 3, wherein said plate has alternating wider and narrower portions.

5. The surgical osteosynthesis plate according to claim 3, wherein the plate comprises two or several plate portions each comprising the diagonal orientation gradient in relation to the direction of a long axis of the plate portion, said plate portions being attached together to one piece.

6. The surgical osteosynthesis plate according to claim 1, wherein said osteosynthesis plate is at a first configuration at a first thermochemical state and is operable to be deformed to a second configuration at said first thermochemical state.

7. The surgical osteosynthesis plate according to claim 6, wherein said osteosynthesis plate is operable to substantially retain said second configuration in conditions of a surgical operation in said first thermochemical state.

8. The surgical osteosynthesis plate according to claim 7, wherein said osteosynthesis plate is operable to substantially change from said second configuration to said first configuration at said first thermochemical state and is operable to be repetitively deformed to different configurations at said first thermochemical state.

9. The surgical osteosynthesis plate according to claim 1, wherein said material has a glass transition temperature and wherein said osteosynthesis plate is initially formable at a first thermochemical state at a temperature below said glass transition temperature to have a first configuration, said osteosynthesis plate being formed from a material which is dimensionally stable in said first configuration at body temperature just after fixation on bone surface in a surgical operation.

10. The surgical osteosynthesis plate according to claim 1, wherein said material from which said bioabsorbable osteosynthesis plate is formed comprises a bioabsorbable polymer, copolymer or polymer alloy, or a mixture of a bioabsorbable polymer, copolymer or polymer alloy and bioceramic or bioactive glass particles or fibers.

11. An implantable bioabsorbable bone stabilization device for stabilizing a plurality of bone portions, said bone stabilization device comprising:
a biocompatible osteosynthesis plate having a first surface, a second surface, a thickness extending between the first surface and the second surface, and a main plane extending between the first surface and the second surface, wherein the plate is formed to one piece from a spirally oriented preform of a material that is oriented parallelly to the main plane of the plate and comprises a continuous gradient of oblique orientation throughout the thickness of the plate, wherein polymer molecules or segments of polymer molecules are aligned in directions of the oblique orientation in said material as a result of solid state deformation of the material, said orientation being oblique in relation to the direction of a reference axis of the plate, and which material is substantially rigid and substantially deformable and dimensionally stable at said first thermochemical state such that the plate is deformable to a deformed state where the plate maintains the deformed state, wherein the first surface has an oblique orientation and the second surface has an oblique orientation such that the oblique orientation of the first surface and the oblique orientation of the second surface are in different directions; and an attachment configured to attach said plate to the plurality of bone portions.

12. The bone stabilization device according to claim 11, wherein said plate has an elongated section defining a first surface and a second surface, whereby said bioabsorbable osteosynthesis plate is operable to stabilize said plurality of bone portions for a period of at least about four to eight weeks following implantation and be substantially completely bioabsorbed after about from one to several years following implantation.

13. The bone stabilization device according to claim 11, wherein the attachment comprises a plurality of fastener openings going through the plate for surgical fasteners being operable to secure said osteosynthesis plate to said plurality of bone portions.

14. The bone stabilization device according to claim 13, wherein at least one of said fastener openings includes a recessed portion operable to receive one of said surgical fasteners.

15. The bone stabilization device according to claim 14, wherein each of said surgical fasteners includes a substantially conical portion operable to engage at least said recessed portion of one of said fastener openings formed in said biocompatible osteosynthesis plate.

16. The bone stabilization device according to claim 11, wherein said material from which said osteosynthesis plate is formed comprises a bioabsorbable polymer, copolymer or polymer alloy, or a mixture of a bioabsorbable polymer, copolymer or polymer alloy and bioceramic or bioactive glass particles or fibers.

* * * * *